United States Patent [19]

Blattner

[11] Patent Number: 5,334,353
[45] Date of Patent: Aug. 2, 1994

[54] MICROPIPETTE DEVICE

[76] Inventor: Frederick R. Blattner, 1547 Jefferson St., Madison, Wis. 53711

[21] Appl. No.: 12,670

[22] Filed: Feb. 3, 1993

[51] Int. Cl.$^5$ .............................................. B01L 3/02
[52] U.S. Cl. ................................... 422/100; 73/864.01; 73/864.11; 73/864.14; 73/864.24; 141/130; 222/148; 222/160; 222/420
[58] Field of Search ............................ 422/100, 104; 73/864.01, 864.11, 864.12, 864.14, 864.15, 864.22, 864.24; 141/130, 275; 222/420, 148, 160, 161

[56] References Cited

U.S. PATENT DOCUMENTS

| | | | |
|---|---|---|---|
| 3,164,304 | 1/1965 | Jager et al. | 222/192 |
| 3,572,400 | 3/1971 | Casner et al. | 141/1 |
| 3,853,008 | 12/1974 | Hoffa et al. | 422/63 X |
| 3,913,636 | 10/1975 | Mochida | 422/100 X |
| 3,915,651 | 10/1975 | Nishi | 73/864.16 |
| 3,960,020 | 6/1976 | Gordon et al. | 73/864.22 |
| 4,094,195 | 6/1978 | Friswell et al. | 73/864.22 X |
| 4,133,918 | 1/1979 | Simms et al. | 427/256 |
| 4,161,508 | 7/1979 | Janchen | 422/100 |
| 4,452,899 | 6/1984 | Alston | 73/864.11 X |
| 4,516,437 | 5/1985 | Pedroso et al. | 73/864.22 |
| 4,570,495 | 2/1986 | Tenada | 422/100 X |
| 4,737,344 | 4/1988 | Koizumi et al. | 73/864.24 X |
| 4,800,762 | 1/1989 | Sugaya | 73/864.24 |
| 4,869,114 | 9/1989 | Kido et al. | 73/864.24 |
| 4,931,257 | 6/1990 | Quenin et al. | 422/104 X |
| 4,989,623 | 2/1991 | Hoffman et al. | 73/864.22 X |
| 5,204,268 | 4/1993 | Matsumoto | 422/100 X |

Primary Examiner—James C. Housel
Assistant Examiner—Maureen M. Wallenhorst
Attorney, Agent, or Firm—Quarles & Brady

[57] ABSTRACT

A fluid delivery device which delivers microliter and sub-microliter volumes by means of a reciprocating force mechanism requires no capillary contact between the delivery system and work surface. Furthermore, a built-in vacuum-based rinse station permits the user to dispense a variety of fluids while avoiding complex and time consuming changes to the fluid delivery system.

8 Claims, 3 Drawing Sheets

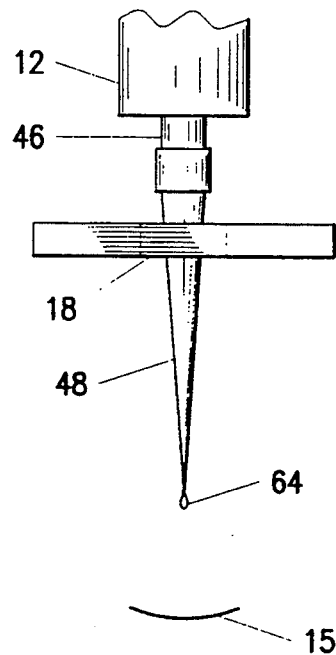
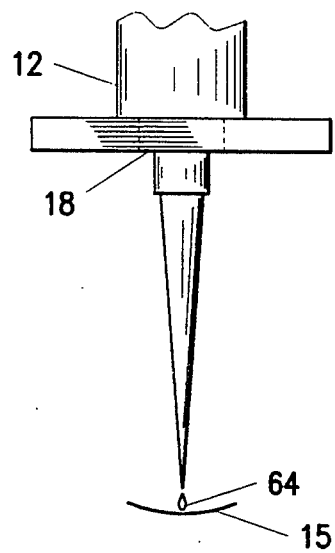
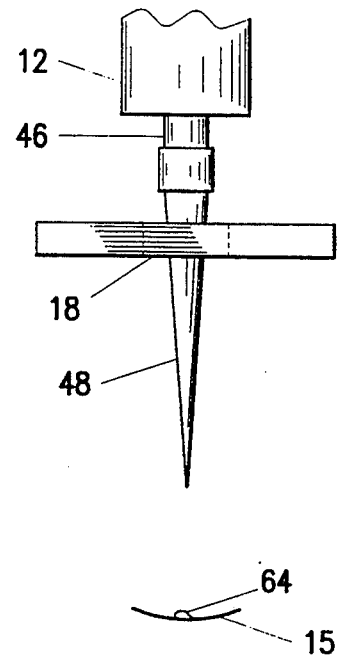
FIG. 3      FIG. 4      FIG. 5
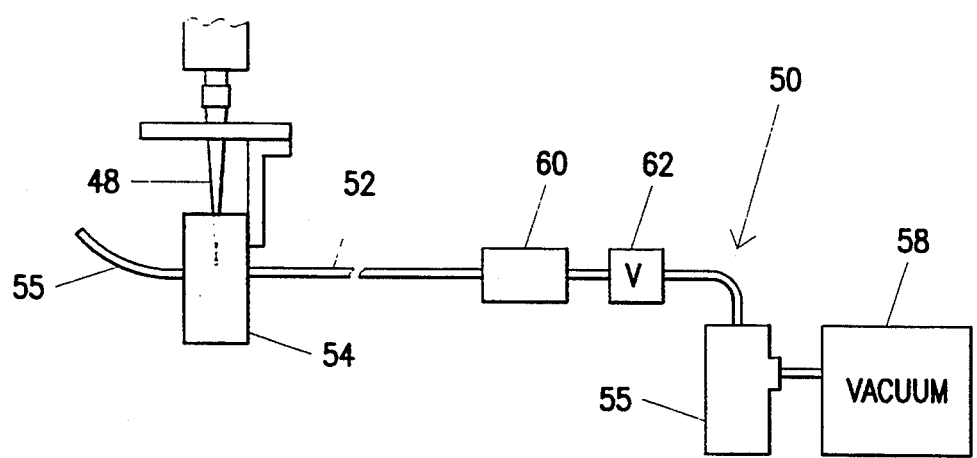
FIG. 6

5,334,353

MICROPIPETTE DEVICE

FIELD OF THE INVENTION

The present invention relates to devices for delivering very small fluid volumes into a receiving tube or well or the like. In particular, the invention relates to devices capable of delivering volumes of one microliter or less. Further, the invention is particularly useful in the field of automated DNA sequence analysis.

BACKGROUND OF THE INVENTION

Several prior art patents disclose devices for dispensing small quantities of liquids. Most rely on capillary action to dispense a drop of liquid from the apparatus to a work surface. Insuring contact between liquid dispenser and work surface has typically required complex adjustment means allowing sufficient contact to transfer the desired amount of material while limiting contact to prevent saturation by capillary action.

In addition, various means for measuring small liquid volumes for delivery have been devised. These include electrically-adjusted syringe barrels, manually-filled capillary pipettes, and repetitive filling of a small notch whose liquid contents flow down a delivery arm and collect as a drop on an arrangement of knobs and slits. Use of each of these devices requires contact with a work surface to ensure complete and accurate transfer of the liquid volume.

One embodiment of an invention in the prior art requires no contact with a work surface to accomplish small volume transfer. The embodiment of FIGS. 6 and 7 of U.S. Pat. No. 3,164,304 (H. N. Jager et al.) can transfer by reciprocating motive force a liquid whose volume is determined by a notch in a plunger rod and which collects at the tip of the plunger rod on an arrangement of knobs and slits. The knobs and slits are required to trap the liquid at the tip of the plunger rod. However, accurately detaching the complete, known volume from the knobs and slits without the help of capillary action is difficult.

In recent years, as the sensitivity of analytical techniques has improved dramatically, it has become desirable to analyze samples of smaller and smaller volume. Both manual and automated devices for delivering small fluid volumes have been devised. When dispensing very small volumes using a manual micropipetter device, one can visually observe whether a small volume has been completely expelled from the fluid delivery system.

This is not the case, however, for automated systems. To effectively exploit automated robotic sample handling technology, one must be quite confident that all required reagents are consistently and accurately dispensed into the reaction vessel. Also, automated sample handlers must avoid cross-contamination between samples. Cross-contamination results when part of a sample deposited in one receiving vessel is picked up by a pipetting device and deposited into a subsequent vessel. Automated systems can yield inexplicable data and erroneous conclusions if the sample analyzed is impure or if all necessary regents are not present in their required amounts. For that reason, it is important that the tip of the automated fluid delivery system not contact the vessel nor the liquid already deposited in the vessel.

Especially when one processes hundreds or thousands of samples, one is also particularly concerned about the cost per sample and therefore desires to use as little of each reagent as possible while at the same time maintaining concentrations of reactants high enough to sustain the reaction, but not so high or so low as to inhibit the reaction.

What is desired is a micropipette device able to deposit the sub-microliter volumes required by modern analytical techniques, yet flexible enough to accurately deliver many different sub-microliter volumes. In addition a desirable device would deliver such small volumes without contacting a work surface and without risking cross-contamination of samples.

SUMMARY OF THE INVENTION

An apparatus which utilizes reciprocating force to propel a sub-microliter volume from the tip of a fluid delivery system into a receiving vessel is disclosed. To overcome the surface tension that would otherwise keep the droplet attached to the tip, a descending slide bearing carrying a dispensing tip with the fluid is abruptly stopped. When the slider bearing is stopped in its downward path, the accelerating liquid droplet at the tip continues its downward acceleration breaking the surface tension that held it in place, until it hits, and is deposited in, the receiving vessel.

It is one object of the present invention to provide a micropipette device capable of accurately and precisely dispensing sub-microliter volumes into a receiving vessel.

It is a further object of the present invention to provide a micropipette device which delivers sub-microliter volumes which would otherwise be retained by surface tension on the micropipette tip.

It is a still further object of the present invention to provide a micropipette device which requires no contact between micropipette tip and work surface and can be rinsed clean without relocation to a rinse station.

Other objects, advantages and features of the present invention will become apparent from the following specification when taken in conjunction with the accompanying drawings.

BRIEF DESCRIPTION OF THE DRAWINGS

The present invention will be described in more detail with reference to the following drawings:

FIGS. 3–5 show a detailed front view of the same embodiment and demonstrate the delivery of a sub-microliter volume into a receiving vessel in accordance with the present invention.

FIG. 6 is a detailed front view of a second embodiment of the present invention which incorporates a shrouded rinse station into the fluid delivery system.

DETAILED DESCRIPTION OF THE INVENTION

Figure 1:
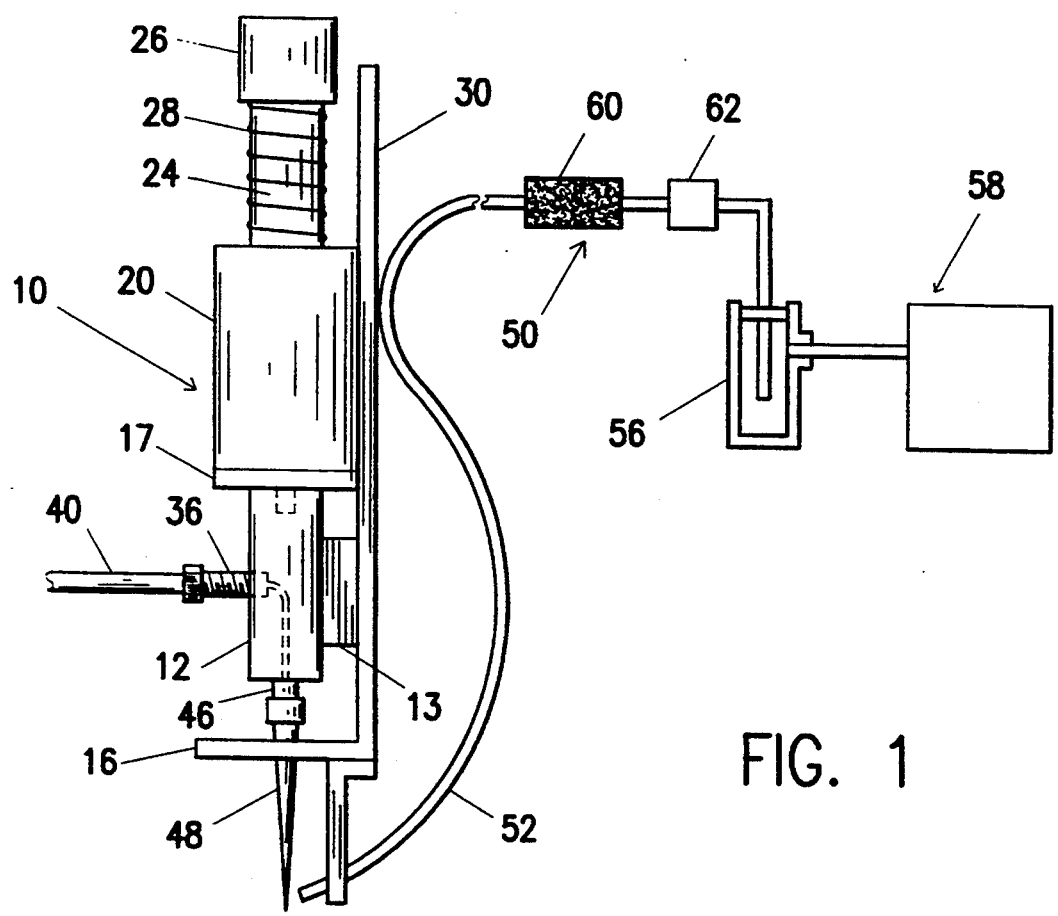
FIG. 1 is a front view of a embodiment of a device for dispensing sub-microliter volumes.

The coupling of advanced analytical techniques and robotic sample handling have increased the desire for accurate, repetitive analysis of a large number of samples. The dramatic increase in sample number has brought to the forefront the need to reduce the space required to process each sample. One successful approach to processing many samples in a small area has been the use of a stationary work space with discrete locations for hundreds of individual samples. Each sample is uniquely accessed by a robotic arm capable of exact positioning on three axes. In certain sampling devices, the sample position changes while the arm remains stationary, though in such devices, four times as much area is needed to process the same number of samples.

As the number of samples in a fixed area has increased, the volume in which a particular reaction is carried out has had to decrease to accommodate increased sample density. At the same time however, the concentration of components, or reagents, in each reaction has had to remain constant. In effect, reactions previously carried out in volumes of 10 to 100 microliters are now being carried in total volumes of just a few microliters. With this decrease in reaction volume has come a corollary benefit which is that entire reaction volumes are now used directly for analysis. It is no longer necessary to discard 80% to 90% of a reaction mixture when only 10% to 20% of the mixture was truly necessary for analysis.

This benefit is particularly striking when one considers the cost of individual reagents in small-volume reactions. Because the absolute and relative concentrations of all reagents in a reaction mixture are critical, large amounts of expensive reagents had to be used even though much of the mixture volume was ultimately discarded. When large reaction volumes were necessary, the expense of wasted reagents was significant.

As it has become feasible to minimize reaction volumes, a different problem has emerged. It has previously been exceedingly difficult to deliver very small volumes with accuracy and precision using a robotic delivery system. Although it might be possible to dilute stocks of particular expensive reagents so that a larger volume containing the desired amount of the reagent could be used, this approach has two drawbacks. First, certain reagents, including some enzymes, must be stored at high concentration to retain full biological activity. Dilution of such reagents, therefore, would again result in as much or more waste than before. Second, the reagent volumes added are still small enough that the error associated with simple robotic dispensing is large. It is well understood that as absolute sample volumes decrease, the error associated with transferring those small volumes increases dramatically. Errors arise from liquid sticking to the walls of delivery systems, from stray liquid sticking to reaction vessel walls, and from difficulties inherent in accurately measuring very small volumes. Further, and most relevant to the problem of dispensing microliter and sub-microliter volumes from a fluid delivery system, is the need to overcome the strong surface tension of very small liquid droplets. With larger drops of more than a microliter the sheer weight of the incipient drop is great enough to cause the drop to fall. In contrast droplets of 1 microliter or less are often not significantly larger than the meniscus at the base of the droplet. Accordingly, additional force is required to direct the small incipient drop from the fluid delivery system outlet.

Figure 2:
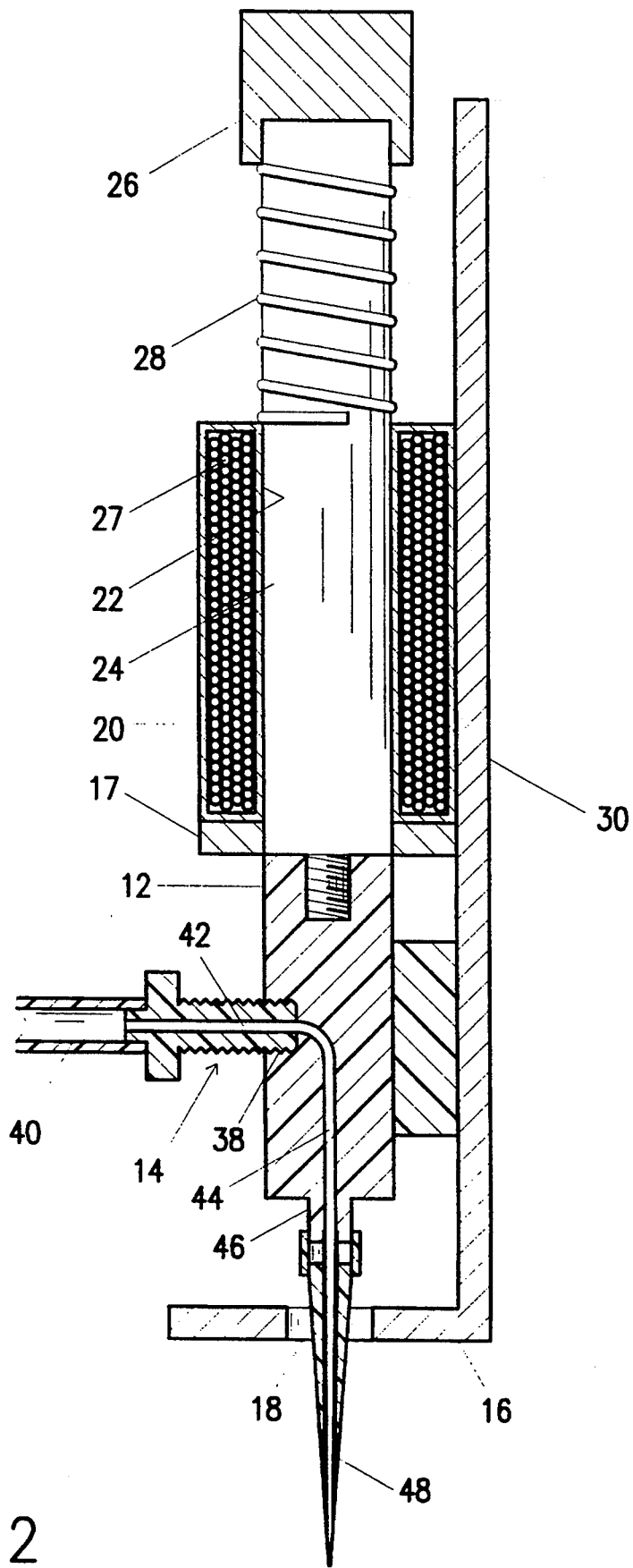
FIG. 2 is a cross-sectional view of a portion of the same embodiment.

Shown in FIGS. 1 and 2 is an overall view of the micropipette device, generally indicated at 10, constructed in accordance with the present invention. A tip holder 12 is mounted on a slide bearing 13 which in turn is mounted on a mounting bracket 30. The tip holder 12 is connected to the shaft 24 of a solenoid, or other linear motive force generator, 20. The central shaft 24 of the solenoid 20 continues upward where it is surrounded by a compression spring 28. A top stop plate 17 and a bottom stop plate 16 limit the linear vertical movement of the tip holder 12. The tip holder 12 carries, at its lowest end, a dispensing tip 48. Generally, the solenoid 20 acts as a linear motor to drive the tip holder 12 downward until it hits the stop 16. When the tip holder 12 hits the stop 16, any liquid at the bottom of the dispensing tip 48 will be knocked off and will fall downward into a waiting receptacle 15. The spring 28 provides the linear force for the reciprocating stroke. By actively pumping desired small volumes of fluid out of the dispensing tip 48 between reciprocations of the solenoid 20, volumes small enough to be held by surface tension on the tip, those volumes can then be delivered into a receptacle without making physical contact with it.

In a preferred embodiment, the motive force generator or solenoid 20 includes an energizable solenoid coil with a central channel 22, the ferromagnetic plunger 24, with a plunger head 26 at one end. The plunger 24 passes coaxially through central channel 22 of the solenoid 20. The compression spring 28 surrounds plunger 24 and is compressed between the plunger head 26 to the top of the solenoid 20. The coil for the solenoid may be actuated via wires 27. Of course, other mechanical devices, such as manual, pneumatic or hydraulic systems, capable of generating a strong linear or even curvilinear downward force followed by reciprocation would work as well. The motive force generator 20 and bottom stop plate 16 are attached to the mounting bracket 30, though the need for support would depend upon the particular design chosen for the motive force generator and bottom stop plate. In this embodiment, reciprocating motive force generator 20 and bottom stop plate 16 are mounted to the mounting bracket 30 by means of metallic fasteners (not shown).

A lower end of the plunger 24 connects to the tip holder 12. The tip holder 12 houses most of fluid delivery system 14 for delivering fluid from a reservoir (not shown) to the receiving receptacle or vessel 15. A fitting 36 through an orifice 38 on one side of the tip holder 12 links tubing 40 to a substantially radial bore 42 in the tip holder 12. Tubing 40 is preferably made of Teflon, though any other flexible, inert tubing material would be adequate. At the other end of tubing 40 is a pump 70 (not shown) capable of dispensing sub-microliter fluid volumes from a fluid reservoir. The pump preferably has a fluid inlet for taking in fluid from a reservoir, and a fluid outlet for dispensing fluid to the fluid delivery system. The pump can be any type of pump with sufficient accuracy and precision to displace sub-microliter volumes. A syringe pump driven by a digitally-controlled stepper motor is particularly well suited to accurate and precise measurements of this kind. A peristaltic pump would suffice as well.

The radial bore 42 is in fluid connection with a central axial vertical needle 44 that descends through the tip holder 12. Attached to the bottom of the tip holder 12 is a collar 46. A micropipette dispensing tip 48 surrounds descending needle 44 and forms a fluid-tight connection with collar 46. In whole, then, fluid delivery system 14 comprises the fluid reservoir (not shown), pump (not shown), the tubing 40, the fitting 36 at the end of the tubing 40, the radial bore 42 to which the fitting 36 connects, the central vertical needle 44 in fluid connection with the radial bore 42 and the micropipette dispensing tip 48. Other arrangements for moving fluid through the tip holder 12 are also envisioned. The precise path of fluid through the tip holder 12 is not critical to the present invention, as long as the needle 44 and the dispensing tip 48 emerge from the bottom of the tip holder 12 and pass through the aperture 18 in the bottom stop plate 16.

The preferred embodiment also incorporates a rinse vacuum system, shown generally in FIG. 1 at 50, which rinses the micropipette tip 48. Rinse tubing 52, with one end located at the bottom of micropipette tip 48, connects at its second end to trap vessel 56 which, in turn, connects by additional rinse tubing 52 to a vacuum source, such as vacuum pump 58. At some point along rinse tubing 52 between micropipette tip 48 and trap vessel 56, an activated charcoal filter 60 may be introduced into the rinse liquid flow path. In addition, an in-line actuatable valve 62 permits control over whether the fluid at tip 48 is exposed to the vacuum of rinse system 50. The valve 62 is preferably electrically-actuated, though a manual, pneumatic or hydraulic valve would also be within the scope of the invention.

In a second embodiment of the rinse vacuum system, a sheath 54 is disposed around micropipette tip 48, as shown in FIG. 6. In addition to the end of the tubing 52, the sheath contains tubing 55 connected to a second rinse liquid source for delivering rinse liquid to the outside of micropipette tip 48.

In operation, the micropipette device is positioned over any type of receiving vessel 15 such as a tube or a well, such that the dispensing tip 48 of fluid delivery system 14 is directly above the desired fluid delivery point as depicted in FIGS. 3-5. The fluid delivery system 14 is typically filled to capacity with fluid. A very small volume of fluid is delivered to the tip 48 by positive displacement of the liquid in the fluid delivery system 14 from a pump (not shown). By precise fluid displacement, the pump forces a small amount of liquid into the already full tubing 40, forcing an incipient droplet 64 of fluid to emerge at the tip 48 of the fluid delivery system 14 as shown in FIG. 3.

When the droplet 64 has appeared at the tip 48, as in FIG. 3, the coil 20 of the motive force generator 20 is electrically energized through the wires 27. The electromagnetic field generated by the energized coil causes the plunger 24 to descend through the channel 22 of the solenoid 20 toward the bottom stop plate 16. The descending plunger 24 pushes the tip holder 12 downward urging the micropipette tip 48 through the aperture 18 toward the receiving vessel 15. Before the plunger 24 / slider bearing 13 / micropipette tip 48 combination can complete its full downward stroke, it is abruptly interrupted by contact between the bottom stop plate 16 and the tip holder 12 as shown in FIG. 4. Although the bottom stop plate 16 stops the movement of the mechanical parts of the embodiment, the momentum of incipient droplet 64 at the dispensing tip 48 propels the droplet 64 in the direction of the plunger 24 movement until the droplet 64 contacts receiving the vessel 15 and settles in place as shown in FIG. 5. When the solenoid 20 is de-energized, the elastic compression spring 28 returns to its uncompressed state, forcing the plunger 24, and the parts connected to the plunger 24, upward and away from the receiving vessel 15. After a complete energizing/de-energizing cycle, the micropipette device may be positioned above another receiving vessel where the cycle may be repeated.

Alternatively, as shown in the embodiment in FIG. 6, the rinse system 50 permits the fluid delivery system 14 to be rinsed by forcing rinse liquid into the tubing 40 and through the fluid delivery system 14. This is useful, for example, to deliver a second liquid to the well. Residue of the first liquid remaining in the system may first be expelled through the tip by the rinse liquid. In such a rinse system, the valve 62 exposes the micropipette tip 48 to a vacuum force only during defined rinse cycles. During a rinse cycle, the force of the vacuum would then draw rinse material away from the tip 48 and would not contaminate receiving vessels beneath the micropipette device. The vacuum pump 58 draws off rinse liquid through the rinse tubing 52 into the trap vessel 56. To rinse the outside of the dispensing tip of this embodiment, tubing 55 connected to a second rinse liquid source (not shown), aimed at the tip, may be incorporated into the rinse station sheath 54. Liquid sprayed through tubing 55 at the outside of the tip will rinse the tip clean and will then be drawn away by the vacuum source. The activated charcoal filter 60 between the sheath 54 and the trap vessel 56 traps radioactive and other wastes for disposal as a small amount of solid waste rather than as liquid waste. Using an integrated rinse station permits extra workspace for samples and reduces cycle time by eliminating movement of the fluid delivery system 14 to a remote rinse station.

The invention described above finds particular application in the field of DNA sequence analysis. Current sequence analysis techniques well known to those skilled in the art represent modifications of a biological reaction that typically occurs in nature at the subcellular level. In brief, a single stranded DNA molecule is used as a template for DNA-polymerase-driven synthesis of a radiolabeled second strand from building blocks known as nucleotides. Four primary nucleotides comprise all DNA molecules. Their chemical names are abbreviated as A,T,C, and G. As the DNA polymerase elongates the second strand, nucleotides are added one at a time. As nucleotides are added to the growing second strand, a double helix forms with the existing template strand by pairwise matching of nucleotides. As such, when an entire second strand has been formed, it is an exact complement to the first strand. The effector of this reaction is a DNA polymerase such as DNA polymerase 1, tag polymerase, or Sequenase.

The ability to harness this reaction for use as an analytical tool in the laboratory depends upon the occasional incorporation of rare modified nucleotides called di-deoxynucleotides which prevent further chain elongation by the DNA polymerase. Instead, when a di-deoxynucleotide is added, a truncated radiolabeled strand of known length is produced. By correlating the chain length with the species of modified nucleotide added to a particular reaction vessel, one can deduce the complementary nucleotide sequence of the template strand.

For purposes of the present invention, it is important only to note that the frequency with which di-deoxynucleotides are incorporated into the growing chain depends in great measure on the relative concentrations of regular nucleotides and di-deoxynucleotides. If too much di-deoxynucleotide is present in a reaction mixture, growing chains will terminate too quickly and one will not obtain a sufficient amount of information from the analytical reactions. In contrast, if too little di-deoxynucleotide is present, elongated chains will be so long as to prevent meaningful analysis by electrophoresis. In addition, the nucleotides, di-deoxynucleotides, radiolabeled nucleotides, and DNA polymerase enzyme are all expensive as a result of the cost of their preparation and purification.

In the research laboratory, automation of small-volume DNA sequencing reactions has dramatically increased the number of samples processed daily and has created a need for an accurate and precise sub-microliter automated micropipette. For instance, large-scale international projects concerning DNA sequence analysis of bacterial, yeast, insect, and human chromosomes demand the eventual automation of all phases of these projects.

The need for a device capable of accurately and precisely dispensing sub-microliter volumes is not limited to the field of DNA sequence analysis. Many other analytical techniques have been automated and can be carried out in reaction volumes of a few microliters. Commercial laboratories in particular often process thousands of human fluid specimens daily. These laboratories would realize a significant savings if they were able to reliably reduce the volume of sample and reagent necessary for each analysis. Furthermore, the ability to perform reactions in smaller volumes increases the likelihood of obtaining meaningful analytical information when only a few microliters of fluid exists for analysis.

Another application of the present invention, distinct but related to the first two applications, is DNA fingerprinting analysis. Used frequently by law enforcement agencies, DNA fingerprinting analysis depends upon the extraction of minute quantities of DNA from blood, saliva, skin, hair, or semen recovered from a crime scene. DNA fingerprinting analysis performed on such samples, and on DNA from suspected criminals, can determine, with a high degree of certainty, whether the recovered DNA was from the tested suspect. Because only very small quantities of DNA are typically recoverable from crime scenes, it is desirable to perform the fingerprinting analysis in a very small volume using minimal amounts of reagents.

It is to be understood that the present invention is not limited to the particular embodiments disclosed herein, nor to the particular uses outlined. The embodiments are intended to be exemplary, rather than limiting and embrace all such variations as come within the scope of the following claims.

I claim:

1. A micropipette device for delivering sub-microliter volumes of fluid into a receptacle, the device comprising;
   a mounting bracket;
   a hollow dispensing tip having a first end and a second end;
   a tip holder holding the dispensing tip at the first end and secured to the mounting bracket in such a way that the tip holder is capable of reciprocal vertical motion;
   a linear motive force generator connected to the mounting bracket and connected to the tip holder to reciprocate the tip holder vertically above the receptacle;
   a fluid tubing adapted for connecting a fluid pump means to the dispensing tip, wherein the fluid pump means forces a sub-microliter droplet of fluid through the tubing and out of the dispensing tip so that the droplet is hold on the second end of the dispensing tip by surface tension; and
   a stop plate located below and in the downward path of travel of the tip holder and fixed in place on the mounting bracket so that vertical downward motion of the tip holder as caused by the linear motive force generator is stopped by the stop plate so as to dislodge the droplet of fluid located on the second end of the dispensing tip so that the droplet falls away from the dispensing tip and drops into the receptacle without the dispensing tip making physical contact with the receptacle.

2. A micropipette device as claimed in claim 1 wherein the linear motive force generator is a solenoid including a shaft driven by a coil, and the shaft of the solenoid is connected to the tip holder.

3. A micropipette device as claimed in claim 2 wherein an extension of the shaft of the solenoid extends out of the solenoid on an end opposite from that connected to the tip holder and wherein a compression spring surrounds and is compressed by downward movement of the extension to provide an upward bias against downward movement of the tip holder.

4. A micropipette device as claimed in claim 3 wherein there is further an upper stop plate mounted on the mounting bracket located above the tip holder to limit upward travel of the tip holder.

5. A micropipette device as claimed in claim 1 wherein the tip holder has a vertically oriented axial needle on the interior thereof through which fluid can flow to the dispensing tip.

6. A micropipette device as claimed in claim 1 wherein the tip holder is connected to the mounting bracket by a slide bearing.

7. A micropipette device as claimed in claim 1 further comprising a rinse station to which the micropipette may be moved for cleaning, the rinse station including a rinse sheath into which the dispensing tip may descend and a vacuum source connected to the sheath.

8. A micropipette device as claimed in claim 7 wherein the rinse station further comprises a rinse liquid source connected to the sheath.

* * * * *